United States Patent
Schlafly et al.

(10) Patent No.: US 10,292,840 B2
(45) Date of Patent: May 21, 2019

(54) BIOMIMETIC PROSTHETIC DEVICE

(71) Applicants: Millicent Kay Schlafly, Santa Cruz, CA (US); Tyagi Ramakrishnan, Tampa, FL (US); Kyle B. Reed, Tampa, FL (US)

(72) Inventors: Millicent Kay Schlafly, Santa Cruz, CA (US); Tyagi Ramakrishnan, Tampa, FL (US); Kyle B. Reed, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/002,853

(22) Filed: Jun. 7, 2018

(65) Prior Publication Data
US 2018/0353309 A1 Dec. 13, 2018

Related U.S. Application Data

(60) Provisional application No. 62/516,333, filed on Jun. 7, 2017.

(51) Int. Cl.
*A61F 2/50* (2006.01)
*A61F 2/60* (2006.01)
(Continued)

(52) U.S. Cl.
CPC .............. *A61F 2/66* (2013.01); *A61F 2/5044* (2013.01); *A61F 2/6607* (2013.01); *A61F 2/72* (2013.01); *A61F 2/602* (2013.01); *A61F 2002/503* (2013.01); *A61F 2002/5038* (2013.01); *A61F 2002/5072* (2013.01);
(Continued)

(58) Field of Classification Search
CPC ................ A61F 2/66; A61F 2002/5072; A61F 2002/7073; A61F 2002/5076; A61F 2002/5078; A61F 2002/5079; A61F 2002/6614; A61F 2002/6621; A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692; A61F 3/00
See application file for complete search history.

(56) References Cited

U.S. PATENT DOCUMENTS 2,430,584 A * 11/1947 Roche ....................... A61F 2/60
                                                              623/46
2,453,969 A * 11/1948 Carter ...................... A61F 2/66
                                                              623/52
(Continued)

OTHER PUBLICATIONS

Adamczyk et al., "Novel method to evaluate angular stiff-ness of prosthetic feet from linear compression tests," Journal of biomechanical engineering, 2013, 135(10): 104502.
(Continued)

*Primary Examiner* — Christie L Bahena
(74) *Attorney, Agent, or Firm* — Michael Best & Friedrich LLP

(57) ABSTRACT

A prosthetic device includes a phalanges portion, a metatarsals portion that is movably coupled to the phalanges portion, an ankle portion that is movably coupled to the metatarsals portion, and a calcaneus portion that is movably coupled to the ankle portion.

9 Claims, 14 Drawing Sheets

(51) Int. Cl.
A61F 2/66 (2006.01)
A61F 2/72 (2006.01)
(52) U.S. Cl.
CPC ............... A61F 2002/6614 (2013.01); A61F 2002/6621 (2013.01); A61F 2002/6635 (2013.01); A61F 2002/6642 (2013.01); A61F 2002/6657 (2013.01)

(56) References Cited

U.S. PATENT DOCUMENTS

| | | | | |
|---|---|---|---|---|
| 2,475,372 | A * | 7/1949 | Catranis | A61F 2/66 623/49 |
| 2,475,373 | A * | 7/1949 | Catranis | A61F 2/66 623/49 |
| 4,547,913 | A | 10/1985 | Phillips | |
| 5,913,902 | A * | 6/1999 | Geible | A61F 2/66 623/52 |
| 6,129,766 | A * | 10/2000 | Johnson | A61F 2/66 623/49 |
| 2009/0204230 | A1* | 8/2009 | Kaltenborn | A61F 2/6607 623/26 |
| 2011/0208322 | A1* | 8/2011 | Rifkin | A61F 2/66 623/55 |
| 2013/0192090 | A1* | 8/2013 | Smith, IV | A43B 13/182 36/103 |

OTHER PUBLICATIONS

Adamczyk et al., "Sensitivity of biomechanical out-comes to independent variations of hindfoot and forefoot stiffness in foot prostheses," Human movement science, 2017, 54:154-171.
Adamczyk et al., "The advantages of a rolling foot in human walking," Journal of Experimental Biology, 2006, 209(20):3953-3963.
Au et al., "Powered ankle-foot prosthesis improves walking metabolic economy," IEEE Transactions on Robotics, 2009, 25(1):51-66.
Au et al., "Powered ankle-foot prosthesis," IEEE Robotics & Automation Magazine, 2008, 15(3): 52-59.
Barocio et al., "Comparison via roll-over shape of the kinematic performance of two low-cost foot prostheses," Biomedical Robotics and Biomechatronics (2014 5th IEEE RAS & EMBS International Conference, 2014, pp. 1028-1032.
Brockett et al., "Biomechanics of the ankle," Orthopaedics and trauma, 2016, 30 (3):232-238.
Caputo et al., "A universal ankle-foot prosthesis emulator for human loco-motion experiments," Journal of biomechanical engineering, 2014, 136(3):035002.
Casillas et al., "Bioenergetic comparison of a new energy-storing foot and sach foot in traumatic below-knee vascular ampu-tations," Archives of physical medicine and rehabilitation, 1995, 76(1):39-44.
Cherelle et al., "Design and validation of the ankle mimicking prosthetic (amp-) foot 2.0," IEEE Transactions on Neural Systems and Rehabilitation Engineering, 2014, 22(1):138-148.
Cherelle et al., "The amp-foot 3, new generation propulsive prosthetic feet with explosive motion characteristics: design and validation," Biomedical engineering online, 2016, 15(3):145.
Crimin et al., "The effect that energy storage and return feet have on the propulsion of the body: a pilot study," Proceedings of the Institution of Mechanical Engineers, Part H: Journal of Engineering in Medicine, 2014, 228(9):908-915.
Crosbie et al., "Effects of reduced ankle dorsiflexion following lateral ligament sprain on temporal and spatial gait parameters," Gait & posture, 1999, 9(3):167-172.
Curtze et al., "Comparative roll-over analysis of prosthetic feet," Journal of biomechanics, 2009, 42(11):1746-1753.
Foot Education, "Bones of the Foot and Ankle," <https://www.footeducation.com/page/bones-of-foot-and-ankle> Feb. 2018.

Gregg et al., "Experimental effective shape control of a powered transfemoral prosthesis," Rehabilitation robotics (ICORR), 2013 IEEE international conference, 2013, pp. 1-7.
Grimmer et al., "A powered prosthetic ankle joint for walking and running," Biomedical engineering online, 2016, 15(3):141.
Hafner et al., "Transtibial energy-storage-and-return prosthetic devices: a review of energy concepts and a proposed nomenclature," Journal of rehabilitation research and development, 2002, 39(1):1.
Handzic et al., "Perception of gait patterns that deviate from normal and symmetric biped locomotion," Frontiers in psychology, 2015, 6:199.
Hansen "Effects of alignment on the roll-over shapes of prosthetic feet," Prosthetics and orthotics international, 2008, 32(4):390-402.
Hansen et al., "Alignment of trans-tibial prostheses based on roll-over shape principles," Prosthetics and orthotics international, 2003, 27(2):89-99.
Hansen et al., "Effective rocker shapes used by able-bodied persons for walking and fore-aft swaying: Implications for design of ankle-foot prostheses," Gait & posture, 2010, 32(2):181-184.
Hansen et al., "Investigations of roll-over shape: implications for design, alignment, and evaluation of ankle-foot prostheses and orthoses," Disability and rehabilitation, 2010, 32(26): 2201-2209.
Hansen et al., "Prosthetic foot principles and their influence on gait," Handbook of Human Motion, 2016, pp. 1-15.
Hansen et al., "Prosthetic foot roll over shapes with implications for alignment of transtibial prostheses," Prosthetics and Orthotics International, 2000, 24(3):205-215.
Hansen et al., "The effective foot length ratio: a potential tool for characterization and evaluation of prosthetic feet," JPO: Journal of Prosthetics and Orthotics, 2004, 16(2):41-45.
Hansen et al., "The effects of prosthetic foot roll-over shape arc length on the gait of trans-tibial prosthesis users," Prosthetics and Orthotics International, 2006, 30(3):286-299.
Hansen et al., "The human ankle during walking: implications for design of biomimetic ankle prostheses," Journal of biomechanics, 2004, 37(10):1467-1474.
Kepple et al., "Relative contributions of the lower extremity joint moments to forward progression and support during gait," Gait & Posture, 1997, 6(1), pp. 1-8.
Koehler-McNicholas et al., "The influence of a hydraulic prosthetic ankle on residual limb loading during sloped walking," PLoS one, 2017, 12(3), p. e0173423.
Kuo et al., "Energetic consequences of walking like an inverted pendulum: step-to-step transitions," Exercise and sport sciences reviews, 2005, 33(2):88-97.
Lamers et al., "The importance of prosthetic ankle range-of-motion for ascending and descending slopes," American Society of Biomechanics, Aug. 2016.
Lemaire et al., "Gait evaluation of a transfemoral prosthetic simulator," Archives of physical medicine and rehabilitation, 2000, 81(6):840-844.
Lundberg et al., "The axis of rotation of the ankle joint," Bone & Joint Journal, 1989, 71(1):94-99.
McGeer et al., "Passive dynamic walking," I. J. Robotic Res., 1990, 9(2):62-82.
Mitchell et al., "A study of the rollover shape in unimpaired persons," JPO: Journal of Prosthetics and Orthotics, 2013, 25(3):138-142.
Mori et al., "The uncanny valley [from the field]," IEEE Robotics & Automation Magazine, 2012, 19(2):98-100.
Muratagic et al., "Combined effects of leg length discrepancy and the addition of distal mass on gait asymmetry," Gait & posture, 2017, 58:487-492.
Nägerl et al., "The upper ankle joint: Curvature morphology of the articulating surfaces and physiological function," Acta of bioengineering and biomechanics, 2016, 18(3).
Olesnavage et al., "Analysis of rollover shape and energy storage and return in cantilever beam-type prosthetic feet," ASME 2014 International Design Engineering Technical Conferences and Computers and Information in Engineering Conference, American Society of Mechanical Engineers, 2014, pp. V05AT08A018-V05AT08A018.

(56) References Cited

OTHER PUBLICATIONS

Paradisi et al., "The conventional non-articulated sach or a multiaxial prosthetic foot for hypomobile transtibial amputees? a clinical comparison on mobility, balance, and quality of life," The Scientific World Journal, 2015.

Pink et al., "Lower extremity range of motion in the recreational sport runner," The American journal of sports medicine, 1994, 22(4):541-549.

Ramakrishnan et al., "Effect of asymmetric knee height on gait asymmetry for unilateral transfemoral amputees," International Journal of Current Advanced Research, 2017, 6(10):6896.

Rouse et al., "Estimation of human ankle impedance during walking using the perturberator robot," Biomedical Robotics and Biomechatronics (BioRob), 2012 4th IEEE RAS & EMBS International Conference, 2012, pp. 373-378.

Rouse et al., "The difference between stiffness and quasi-stiffness in the context of biomechanical modeling," IEEE Transactions on Biomedical Engineering, 2013, 60(2):562-568.

Sam et al., "Characterisation of prosthetic feet used in low-income countries," Prosthetics and orthotics international, 2004, 28(2):132-140.

Sam et al., "The 'shape&roll' prosthetic foot: I. design and development of appropriate technology for low-income countries," Medicine, Conflict & Survival, 2004, 20(4):294-306.

Schlafly et al., "3D Printed Passive Compliant and Articulating Prosthetic Ankle Foot," Proceedings of the ASME International Mechanical Engineering Congress and Exposition, IMECE, 2017.

Schmalz et al., "Energy expenditure and biomechanical characteristics of lower limb amputee gait: The influence of prosthetic alignment and different prosthetic components," Gait & posture, 2002, 16(3):255-263.

Shamaei et al., "On the mechanics of the ankle in the stance phase of the gait," Engineering in Medicine and Biology Society, EMBC, 2011 Annual International Conference of the IEEE, 2011, pp. 8135-8140.

Shell et al., "The effects of prosthetic foot stiffness on transtibial amputee walking mechanics and balance control during turning," Clinical Biomechanics, 2017, 49:56-63.

Shepherd et al., "Design of a quasi-passive ankle-foot prosthesis with biomimetic, variable stiffness," Robotics and Automation (ICRA), 2017 IEEE International Conference, 2017, pp. 6672-6678.

Stauffer et al., "Force and motion analysis of the normal, diseased, and prosthetic ankle joint," Clinical orthopaedics and related research, 1977, 127, pp. 189-196.

Su et al., "The effects of increased prosthetic ankle motions on the gait of persons with bilateral transtibial amputations," American journal of physical medicine & rehabilitation/Association of Academic Physiatrists, 2010, 89(1), p. 34.

Torricelli et al., "Human-like compliant loco-motion: state of the art of robotic implementations," Bioinspiration & biomimetics, 2016, 11(5):051002.

Tsai et al., "Swing phase simulation and design of above knee prostheses," Journal of Biomechanical Engineering, 1986, 108(1):65-72.

Van Keeken et al., "Principles of obstacle avoidance with a transfemoral prosthetic limb," Medical Engineering and Physics, 2012, 34(8):1109-1116.

Van Keeken et al., "Stabilizing moments of force on a prosthetic knee during stance in the first steps after gait initiation," Medical Engineering and Physics, 2012, 34(6):733-739.

Vanicek et al., "Kinematic adaptations to a novel walking task with a prosthetic simulator," JPO: Journal of Prosthetics and Orthotics, 2007, 19(1):29-35.

Ventola, "Medical applications for 3d printing: current and projected uses," Pharmacy and Therapeutics, 2014, 39(10):704-711.

Ventura et al., "The effect of prosthetic ankle energy storage and return properties on muscle activity in below-knee amputee walking," Gait & posture, 2011, 33(2):220-226.

Ventura et al., "The effects of prosthetic ankle dorsiflexion and energy return on below-knee amputee leg loading," Clinical Biomechanics, 2011, 26(3):298-303.

Versluys et al., "From conventional prosthetic feet to bionic feet: a review study," Biomedical Robotics and Biomechatronics, 2008. BioRob 2008. 2nd IEEE RAS & EMBS International Conference, 2008, pp. 49-54.

Vickers et al., "Elderly unilateral transtibial amputee gait on an inclined walkway: a biomechanical analysis," Gait & posture, 2008, 27(3):518-529.

Wagner et al., "Motion analysis of sach vs. flex-foot in moderately active below-knee amputees," Clin Prosthet Orthot, 1987, 11(1):55-62.

Webber et al., "The role of plantigrady and heel-strike in the mechanics and energetics of human walking with implications for the evolution of the human foot," Journal of experimental biology, 2016, 219(23):3729-3737.

Ziegler-Graham et al., "Estimating the prevalence of limb loss in the united states: 2005 to 2050," Archives of physical medicine and rehabilitation, 2008, 89(3):422-429.

Ramakrishnan. Asymmetric unilateral transfemoral prosthetic simulator. University of South Florida, 2014.

\* cited by examiner

| | |
|---|---|
| $r_1 =$ | Distance from the center of curvature of the rocker to the ankle marker |
| $r_2 =$ | Radius of the rocker |
| $r_5 =$ | Distance from the ankle marker to the arm center of rotation |
| $r_6 =$ | Distance from the arm center of rotation to the point of contact with the ground |
| $\theta_2 =$ | -90° |
| $\theta_4 =$ | 90° |
| $\theta_3 =$ | 0, 180 |
| $\theta_7 =$ | 0, 180 |

FIG. 18: Fixed Geometric Parameters of CAPA Foot

| | |
|---|---|
| Vector Sum | $\vec{R_1} = \vec{R_2} + \vec{R_3} + \vec{R_4}$ |
| Position | $r_1 e^{i\theta_1} = r_2 e^{i\theta_2} + r_3 e^{i\theta_3} + r_4 e^{i\theta_4}$ |
| X-Direction | $r_1 \cos(\theta_1) = r_2 \cos(\theta_2) + r_3 \cos(\theta_3) + r_4 \cos(\theta_4)$ |
| Y-Direction | $r_1 \sin(\theta_1) = r_2 \sin(\theta_2) + r_3 \sin(\theta_3) + r_4 \sin(\theta_4)$ |
| Velocity | $r_1 i \dot{\theta}_1 e^{i\theta_1} = 0 + \dot{r}_3 e^{i\theta_3} + \dot{r}_4 e^{i\theta_4}$ |
| X-Direction | $-r_1 \dot{\theta} \sin(\theta_1) = \dot{r}_3 \cos(\theta_3) + \dot{r}_4 \cos(\theta_4)$ |
| Y-Direction | $r_1 \dot{\theta} \cos(\theta_1) = \dot{r}_3 \sin(\theta_3) + \dot{r}_4 \sin(\theta_4)$ |

FIG. 19: Ankle Loop Equations

| | |
|---|---|
| Vector Sum | $0 = \vec{R_4} + \vec{R_5} + \vec{R_6} + \vec{R_7}$ |
| Position | $r_4 e^{i\theta_4} + r_5 e^{i\theta_5} + r_6 e^{i\theta_6} + r_7 e^{i\theta_7} = 0$ |
| X-Direction | $r_4 \cos(\theta_4) + r_5 \cos(\theta_5) + r_6 \cos(\theta_6) + r_7 \cos(\theta_7) = 0$ |
| Y-Direction | $r_4 \sin(\theta_4) + r_5 \sin(\theta_5) + r_6 \sin(\theta_6) + r_7 \sin(\theta_7) = 0$ |
| Velocity | $\dot{r}_4 e^{i\theta_4} + r_5 i \dot{\theta}_5 e^{i\theta_5} + r_6 i \dot{\theta}_6 e^{i\theta_6} + \dot{r}_7 e^{i\theta_7} = 0$ |
| X-Direction | $\dot{r}_4 \cos(\theta_4) - r_5 \dot{\theta} \sin(\theta_5) - r_6 \dot{\theta} \sin(\theta_6) + \dot{r}_7 \cos(\theta_7) = 0$ |
| Y-Direction | $\dot{r}_4 \sin(\theta_4) + r_5 \dot{\theta} \cos(\theta_5) + r_6 \dot{\theta} \cos(\theta_6) + \dot{r}_7 \sin(\theta_7) = 0$ |

FIG. 20: Arm Loop Equations

|  | Plantar flexion $\left(\frac{N}{deg}\right)$ | Dorsiflexion $\left(\frac{N}{deg}\right)$ |
| --- | --- | --- |
| CAPA Small Radius Long Moment Arm Compliant | 1.9 | 1.8 |
| CAPA Small Radius Long Moment Arm Stiff | 3.8 | 3.5 |
| CAPA Large Radius Short Moment Arm Compliant | 1.9 | 2.2 |
| CAPA Large Radius Short Moment Arm Stiff | 3.8 | 4.5 |

FIG. 21: Effective Rotational Stiffness Values of CAPA Foot at the End of the Moment Arm

| Parameter | Geometric Equivalent | Effect on roll over shape |
| --- | --- | --- |
| $\vec{R_1}(r_1, \theta_1)$ | Vector from the center of curvature of the rocker to the ankle marker | Larger $r_1$ – ROC increases, $\theta_1 = 270°$ – largest ROC, $\theta_1 = 180°$ – largest $X_c$ |
| Heel $\vec{R_5}(r_5, \theta_5)$ | Vector from the ankle marker to the heel arm center of rotation | No major effect |
| Heel $\vec{R_6}(r_6, \theta_6)$ | Vector from the heel arm center of rotation to the point of contact with the ground | Larger $r_6$ – smaller ROC and $X_c$, $\theta_6$ – No effect |
| Foot $\vec{R_5}(r_5, \theta_5)$ | Vector from the ankle marker to the foot arm center of rotation | Larger $r_5$ – ROC increases and $X_c$ decreases, As $\theta_5$ approached 180°, $X_c$ increases and ROC decreases |
| Foot $\vec{R_6}(r_6, \theta_6)$ | Vector from the foot arm center of rotation to the point of contact with the ground | Larger $r_6$ – smaller ROC and $X_c$, $\theta_6$ – No effect |

FIG. 22: Summary of the Effect That Changing Individual Parameters Have on the Roll Over Shape Radius of Curvature (ROC) and Horizontal Center of Curvature ($X_c$)

BIOMIMETIC PROSTHETIC DEVICE

CROSS-REFERENCE TO RELATED APPLICATION(S)

This application is a non-provisional of and claims the benefit of U.S. Provisional Patent Application No. 62/516,333, filed on Jun. 7, 2017, the contents of which are incorporated herein by reference.

BACKGROUND OF THE INVENTION

The human ankle is crucial to mobility as it counteracts the forces and moments created during walking. Currently there are nearly 2 million people living with limb loss in the United States. Many of these individuals are either transtibial (below knee) or transfemoral (above knee) amputees and require an ankle-foot prosthesis for basic mobility. While there are an abundance of options available for individuals who require an ankle-foot prosthesis, these options fail to mimic an intact ankle when it comes to key evaluation criteria such as range of motion, push-off force, and roll over shape.

The simplest type of ankle-foot prosthesis is the conventional non-articulating SACH (Solid Ankle Cushioned Heel) foot shown in FIG. 6. The SACH foot is able to closely resemble the shape of an actual foot and provides the user with some cushioning during movement. However, it is unable to provide the range of motion and energy return of an intact ankle. Regardless, many less active amputees prefer the SACH foot because of the greater control it gives the amputee.

Unlike the SACH foot, the dynamic response ankle-foot shown in FIG. 11 stores energy during the beginning of the gait cycle and uses the stored energy to propel the foot forward. Also called ESR for Energy Storing and Returning, the energy storage mechanism of the dynamic response ankle-foot is similar to the role of the Achilles tendon. During gait, the Achilles tendon is stretched and stores potential energy that is released during push-off. The energy storage mechanism in dynamic response feet are typically primarily weight activated. This means the prosthetic will store energy while the individual is standing unlike an able-bodied ankle. Despite this difference, the dynamic response ankle-foot provides some resistance to movement similar to that of an intact ankle.

Dynamic response feet can be further classified as either passive or active (microprocessors). Because the energy produced by the ankle joint during average walking speeds is almost completely self-sustaining with no net external energy loss, there is the potential for a purely mechanical mechanism such as the dynamic response ankle to generate the forward motion necessary for an able-bodied gait. However, for speeds faster than normal walking, passive systems are not capable of fully emulating an intact ankle because a positive net external energy is produced by the ankle. The use of an active ankle foot prosthesis for faster speeds may be necessary in the future, but current design limitations make this application less than ideal. An active ankle-foot prosthesis can be over twice as heavy as a conventional prosthesis, are expensive, and experience hardware and control issues adjusting to different speeds. Fundamentally, active prosthetic ankle-feet operate using preplanned kinematic trajectories as opposed to the impedance control mechanism of a human ankle. Finally, while still operating as an ESR system, active ankle-foot prostheses are difficult to customize or match biomimetically in size and weight.

The amount of energy stored in the prosthesis is dependent on the stiffness. Increasing the stiffness will increase the propulsion forces, however, it simultaneously decreases the range of motion (ROM) of the ankle. The ankle joint has a ROM from about 45° plantar flexion to 20° dorsiflexion. Forced to make a choice between propulsion forces and range of motion, many ankle-foot prostheses have only been designed for the ROM that is experienced during gait on an even surface, a value of no more than 30°. While this may seem sufficient as the ROM of the ankle remains consistent with changes in speed, a study looking at individuals with limited ankle ROM due to a sprain showed that ankle ROM does impact gait symmetry in regards to step length and step time. Additionally, ankle ROM is important for walking on sloped surfaces as it helps accommodate for movement about different equilibrium positions.

While both the kinematics and kinetics of an intact ankle are important to its functionality, so far it has been impossible for a passive prosthetic ankle-foot to mimic both. There exists a discrepancy between design changes that improve the kinematics and kinetics. The effect of increasing stiffness is an example of this discrepancy. In an able-bodied ankle, the relationship between angle and push-off moment is linear. However, most prostheses are built with a stiff plastic board that resembles a cantilever beam. A rudimentary knowledge of cantilever beams tells us that the linear relationship between deflection and force is restricted to small deflections and much less than the ankle angle experienced by an able-bodied individual. The stiffness of the foot also impacts the location of the ground reaction forces, and therefore the rollover shape as discussed below. Olesnavage and Winter noticed this effect and suggested the use of a rigid constraint to prevent the foot from over-deflecting.

Recent research in active prostheses has been able to demonstrate the effectiveness of applying a torque that is linear with ankle angle in single subject experiments in a lab environment. Caputo and Collins used a Universal Ankle-Foot Prosthesis Emulator that determined the desired torque by a piecewise linear function in 2014. A team at the Robotics and Multibody Mechanics Research Group at the Vrije Universiteit Brussel is making progress in mimicking both kinematics and kinetics in the development of the actuated prosthetic AMP-Foot. Although not explicitly stated, one of the major changes between the AMP-Foot 2.0 tested in 2014 and the AMP-Foot 3.0 in 2016 was a linear relationship between torque and ankle during initial contact to flat foot. The change resulted in a curve that better mimics an intact ankle as provided by Winter's data and an extra 5 Joules of energy storage. It is interesting to note that the strategy used in the design of active prosthetics to achieve both push-off and range of motion in fast walking speeds is to effectively increase stiffness with ankle angle. While this strategy has been applied to the design a quasi-passive prosthetic ankle-foot that increases the stiffness with ankle angle using a cam-based transmission and an active sliding support beneath the leaf spring, the strategy cannot be used in a completely passive prosthesis because it requires positive work to be done by the prosthetic, nor should it be necessary for normal walking speeds.

Hansen developed a characteristic of gait called the roll over shape that incorporates both the kinematics and kinetics. The roll over shape is created by plotting the center of pressure during a step in a shank-based coordinate system. Recent research, summarized by Hansen and Childress, has found that "roll-over shapes in able-bodied subjects do not change appreciably for conditions of level ground walking, including walking at different speeds, while carrying different amounts of weight, while wearing shoes of different heel heights, or when wearing shoes with different rocker radii". This suggests that able-bodied individuals will alter their ankle kinematics to preserve their roll-over shape. However, amputees do not have the adaptive control that an able-bodied individual has over their roll-over shape. Therefore, the design of the prosthetic predominantly controls the roll-over shape an amputee will produce. As a result, it has become a method to evaluate prosthetics. However, while the roll over shape demonstrates the relationship between kinematics and kinetics, it is not directly impacted by magnitude. Other evaluation methods are necessary to determine the late stance push-off.

SUMMARY OF THE INVENTION

Human gait has evolved to maximize energy efficiency through adaptations such as beginning the gait cycle with heel strike. The role of the ankle joint is crucial to healthy and efficient gait. As a result, individuals lacking an ankle consume over 20% more oxygen than able-bodied individuals. The prospect of human augmentation has motivated prosthetic designs that sacrifice characteristics of the evolved able-bodied ankle for enhanced functionality in a specific area. However, for unilateral amputees in particular, any deviation in functionality from the able-bodied ankle causes gait asymmetry and requires extra effort by the amputee to compensate. By taking a more biomimetic approach to the prosthetic design, energy consumption required by amputees can be decreased and quality of life improved. Therefore, the ideal prosthetic can be defined in its ability to replace the able-bodied limb in size, shape, and most importantly, functionality. Prosthetic ankles can be evaluated by their ability to mimic the behavior of an intact ankle with regards to kinematics, kinetics, and roll over shape.

In order to mimic the functionality of the ankle during gait, it is necessary to identify the characteristics of an able-bodied gait that cannot be achieved without the ankle. Because the SACH foot provides very little ankle functionality, the gait produced by the SACH foot was compared to an able-bodied gait to determine the role of the ankle joint during gait. Data was used from an experimental study looking at the effect that knee height has on the gait of a transfemoral amputee. Five subjects were asked to walk at a self-selected speed for two minutes and for at least one minute wearing the prosthetic simulator with the SACH foot shown in FIG. 6.

The gait cycle is used to describe and graph behavior during a typical step. The gait cycle begins in stance phase by the heel initially striking the ground and exerting a braking force. The beginning 60% of the gait cycle is stance phase where the foot is in contact with the ground. As the step and stance phase proceeds, the foot becomes further dorsiflexed. In dorsiflexion the toes are pointed upward from the neutral position. As stance phase ends, the foot pushes off to propel the individual forward. During push-off the foot is in plantar flexion with the toes pointed downward. The gait cycle ends with swing phase to repeat again when the heel is returned to the frontmost position and strikes the ground. The sagittal plane divides the right and left hand sides of the body. Most of the analysis throughout this paper is performed in the sagittal plane.

The kinematics of the ankle can be described by its angle during the gait cycle. The range of motion of the ankle during gait on an even surface is no more than 30° and remains consistent with changes in speed. The ankle angles shown in FIG. 12 supports previous findings. However, the full range of motion of the ankle joint is from about 45° plantar flexion to 20° dorsiflexion. In conclusion, the "ideal" prosthetic ankle should have a range of motion of about 45° plantar flexion to 20° dorsiflexion but exhibit a range of motion of less than 30° during gait.

FIGS. 13 and 14 show the ground reaction forces at each subject's normal walking speed plotted against gait cycle in comparison with an individual wearing the prosthetic simulator with the SACH foot. The maximum vertical forces of the able-bodied individuals in FIG. 13 exhibit two distinctive peaks that are not seen in the ground reaction forces for the SACH foot. The maximum push-off forces of the SACH foot in FIG. 14 are much less than that produced by an able-bodied gait. Some subjects are able to compensate for the loss of the ankle's contribution to push-off better than others. For example, Subject 4 has the lowest maximum able-bodied push-off force and the highest maximum SACH foot push-off force. In contrast, Subject 1 has the second highest maximum able-bodied push-off force and the lowest maximum SACH foot push-off force.

To establish the roll over shape of an able-bodied individual, the center of pressure is plotted in a shank-based coordinate system during stance phase in FIG. 15. Stance phase is established when over 50% percent of each subject's body weight is on the right platform. The inverted pendulum model approximation and a study of 16 subjects performed by Mitchell et al. shows that the ideal roll over shape radius is approximately 20% body height. As all five subjects were between 177-187 cm in height, literature would suggest the best fit radius to be 35.4-37.4 cm. The roll over shape of the five able-bodied subjects shown in FIG. 15 has a best fit radius of 38.8 cm and is consistent with the study performed by Mitchell et al.

By comparing the roll over shapes of physically impaired and able-bodied individuals, characteristics such as a larger radius of curvature (R), a longer arc length, and a longer roll over shape in the X-direction (EFL, Effective Foot Length), have been determined to be preferable. Similarly, a positive x-coordinate center of curvature ($X_c$) is an observable characteristic of able-bodied roll over shapes and better prosthetics. S. Miff et al. found that a $X_c$ behind the ankle occurs during gait initiation, a $X_c$ in front of the ankle occurs during gait termination, and the $X_c$ is at a neutral position during steady state gait. The roll over shape of ankle-foot prostheses that lack adequate push-off prematurely curve upwards resulting in a smaller best fit radius, arc length, EFL, and center of curvature in the horizontal direction ($X_c$). The center of curvature in the horizontal direction ($X_c$) of the roll over shape of all five subjects shown in FIG. 15 is positive as well with a value of 2.02 cm, but smaller than the center of curvature for the SACH foot roll over shape (29.3 cm).

While the roll over shape is usually modeled as a circular arc, it has also been modeled as a second order polynomial. A second order polynomial was found to fit the roll over shape of the CAPA foot better and used to determine the radius of curvature, $X_c$, and forward length in the x-direction.

The present invention relates to prosthetic devices. In particular, the present invention relates to a compliant and articulating prosthetic ankle foot.

In one aspect, a prosthetic device includes a phalanges portion, a metatarsals portion that is movably coupled to the phalanges portion, an ankle portion that is movably coupled to the metatarsals portion, and a calcaneus portion that is movably coupled to the ankle portion.

In another aspect, a prosthetic device includes a phalanges portion, a metatarsals portion coupled to the phalanges portion, an ankle portion coupled to the metatarsals portion, and a calcaneus portion coupled to the ankle portion. At least one biasing member is configured to bias at least one of the phalanges portion, the metatarsals portion, the ankle portion, and the calcaneus portion in a rotational direction.

In yet another aspect, a prosthetic ankle foot includes an ankle portion, a metatarsals portion, a calcaneus portion, and a phalanges portion. The ankle portion includes a first end with a connector and a second end with a rocker. The first end is opposite the second end. The metatarsals portion is rotatably coupled to the ankle portion by a first biasing member. The calcaneus portion is rotatably coupled to the ankle portion by a second biasing member. The metatarsals portion and the calcaneus portion are coupled to the ankle portion on opposite sides of the rocker. The phalanges portion is rotatably coupled to the metatarsals portion by a third biasing member.

BRIEF DESCRIPTION OF THE DRAWINGS

FIG. 18 is a table illustrating fixed geometric parameters used in FIGS. 16 and 17.

FIG. 19 is a table illustrating ankle loop equations governing the vector loops of FIG. 16.

FIG. 20 is a table illustrating arm loop equations governing the vector loops of FIG. 16.

FIG. 21 is a table illustrating effective rotational stiffness values for the prosthetic device of FIG. 1.

FIG. 22 is a table illustrating the effects that individual parameters have on a roll over shape radius of curvature.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The human ankle allows for rotational movement that resembles a ball and socket joint and provides the support for ground reaction forces up to ten times an individual's body weight. During gait, contraction of the plantar flexors act to create a moment (in N-m) about the ankle joint that is both twice an individual's body weight and twice the moment created about either the knee or hip. Additionally, the forward motion that occurs during gait is generated primarily by the plantar flexor muscles about the ankle joint. Thus, it is essential for an ankle foot prosthetic to mimic the propulsion forces created by the ankle to produce a natural gait.

Figure 1:
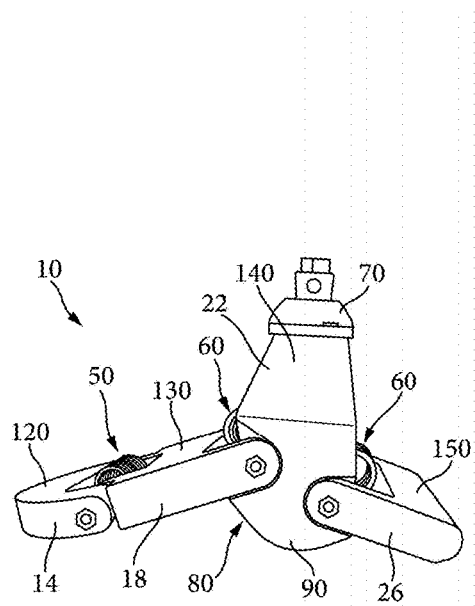
FIG. 1 is a side view of a prosthetic device according to one embodiment of the invention.
Figure 2:
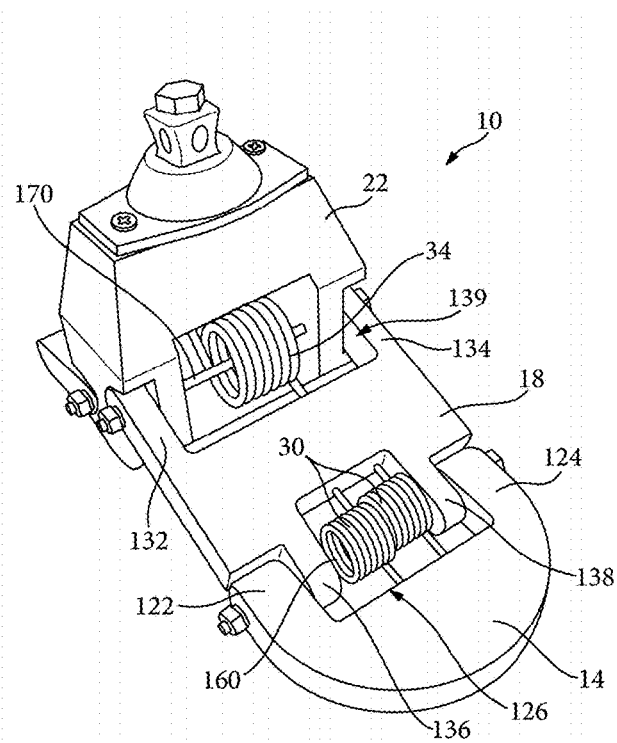
FIG. 2 is a perspective view of the prosthetic device of FIG. 1.
Figure 3:
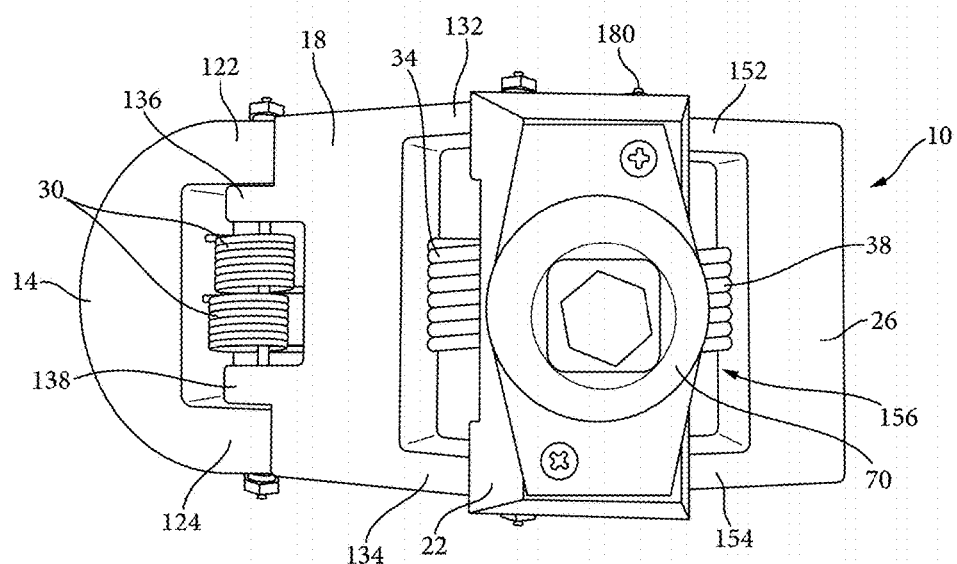
FIG. 3 is a top view of the prosthetic device of FIG. 1.

With reference to FIGS. 1-3, a prosthetic device (i.e., ankle foot) 10 addresses some of the flaws in previous ankle prosthetic systems and better mimics a healthy ankle. The prosthetic device 10 may provide advantages over previous ankle prosthetic systems, such as being less expensive, allowing for personalization, and allowing for sloped walking. The prosthetic device 10 is easily and inexpensively customized using 3D printing to better fit individuals of different sizes, natural gait patterns, and personal preferences. The prosthetic device 10 according to one embodiment and illustrated in FIGS. 1-3 comprises Acrylonitrile Butadiene Styrene (ABS) or Polylactic Acid (PLA) with 100% infill. The device utilizes a rapidly advancing field and models, in additional or alternative embodiments can be constructed from any suitable material such as materials that are lighter, more durable, and stronger than ABS or PLA. The visual appeal of the prosthetic device 10 can be optimized with 3D printing to avoid the uncanny valley and develop a prosthetic that has both a large degree of human likeness and familiarity.

With continued reference to FIGS. 1-3, the prosthetic device 10 includes a first or phalanges portion 14, a second or metatarsal portion 18, a third or ankle portion 22, and a fourth or calcaneus portion 26. In one construction, each of the portions of the prosthetic device 10 is printed from a 3D printer. In the illustrated embodiment, the phalanges portion 14, includes a main body 120 having a first arm 122 extending from the main body 120 at a first end and a second arm 124 extending from the main body 120 at a second end opposite the first end. The main body 120 is curved or contoured at is front face and defines a recess 126 between the first arm 122 and the second arm 124 to accommodate one or more biasing members or springs 30. The phalanges portion 14 is movably (e.g., rotatably) coupled to the metatarsal portion 18 by the spring(s) 30. In the illustrated embodiment, the spring(s) 30 comprise two 1.18 N-m 180° steel torsion spring(s), although in other or additional embodiments fewer or greater spring(s) having different values and materials may be used.

In the illustrated embodiment, the metatarsals portion 18 includes a main body 130 having a first arm 132 extending from the main body 130 at a first end and a second arm 134 extending from the main body 130 at a second end opposite the first end. The main body 130 also includes a third arm 136 and a fourth arm 138 extending from a face of the main body 130, which are received within the recess 126 of the phalanges portion 14. The main body 130 also defines a recess 139 between the first arm 132 and the second arm 134 to accommodate one or more biasing members or springs 34. The ankle portion 22 is movably (e.g., rotatably) coupled to the metatarsal portion 18 by the spring(s) 34.

In the illustrated embodiment, the ankle portion 22 has a main body 140 which includes a rocker 90 (FIGS. 1 and 9A-10B) with a radius that is similar to the Talus bone in an able-bodied ankle. In another embodiment, the rocker 90 includes a radius that is approximately 0.3 times a total leg length. In still another embodiment, the rocker 90 includes a radius that is approximately 20% of an individual's total height. The ankle portion 22 also includes platforms 94 (FIGS. 9A-10B) which define ends of the rocker 90 (i.e., the rocker 90 extends between the platforms 94). The first arm 132 and the second arm 134 of the metatarsals portion 18 are movably (e.g., rotatably) coupled to one platform 94.

In the illustrated embodiment, the calcaneus portion 22 includes a main body 150 having a first arm 152 extending from the main body 150 at a first end and a second arm 152 extending from the main body 150 at a second end opposite the first end. The main body 150 is rounded at is front face and defines a recess 156 between the first arm 152 and the second arm 154 to accommodate one or more biasing members or spring(s) 38. The first arm 152 and the second arm 154 of the calcaneus portion 26 are movably (e.g., rotatably) coupled to other platform 94 by the spring(s) 38.

In the illustrated embodiment, the springs 34, 38 each comprise 5.0 N-m 120° steel torsion springs, although in other or additional embodiments fewer or greater springs having different values and materials may be used. Each of the springs 30, 34, 38 includes a pair of arms. The arms of the springs 30, 34, 38 are positioned in holes formed in the portions 14, 18, 22, 26. The prosthetic device 10 also includes eighth inch (3.175 mm) stainless steel shafts 160, 170, 180 (i.e., joint elements) at each of the movably coupled portions (e.g., shaft 160 extends between the phalanges portion 14 and the metatarsals portion 18, shaft 170 extends between the metatarsals portion 18 and the ankle portion 22, and shaft 180 extends between the ankle portion 22 and the calcaneus portion 26). The shafts 160, 170, 180 extend through the respective springs 30, 34, 38 and for the entire width of the prosthetic device 10. Choices in shaft size and direction of 3D printing were made with tear-out failure in mind.

The device 10 also includes a carbon-fiber and nylon composite pyramid-shaped head 70 (or other suitable connector) that is coupled (i.e., bolted or otherwise secured) onto the ankle portion 22 of the prosthetic device 10. In other constructions, the head 70 may comprise suitable alternative shapes and is not limited to the particular shape shown in the figures. The head 70 is attachable to other prosthetic pieces or structures (i.e., may be a universal adapter). Finally, the prosthetic device 10 further includes a traction material 80 such as rubber that was painted onto a bottom surface of the prosthetic device 10. Any suitable traction material can be used.

The relative motion of the portions 14, 18, 22, 26 allows for the prosthetic device 10 to experience the full range of motion of the ankle joint. Platforms prevent excess flexion for greater stability. The prosthetic device 10 is classified as a type of dynamic response foot as it stores potential energy at the springs 30, 34, 38 and releases that energy to assist in forward movement. Unlike the majority of current ankle systems that only mimic the ESR that occurs in the Achilles tendon for plantar flexion, the prosthetic device 10 stores energy at each spring to mimic toe flexion at location 50 in FIG. 1 and both plantar flexion and dorsiflexion at location 60. The springs 30, 34, 38 mimic the energy storage function of ankle tendons and provide a necessary push off force for forward motion. The springs 30, 34, 38 can be easily replaced with springs of different stiffnesses (not shown) for users with different walking speeds and body weights.

During the unloading phase of a healthy ankle, there is a linear increase in the moment exerted by the ankle. This can be emulated by a torsion spring because the force exerted by a spring also follows a linear profile and the angular velocity of an ankle is constant about a point. The springs can be easily replaced, allowing the same ankle foot prosthetic to accommodate different applications or speeds. Each individual can adjust the stiffness to what would best reduce their metabolic cost of walking. Optimizing the stiffness is important to provide a balance between the greater propulsive forces provided by stiffer designs and the stabilization stiffer designs require.

Figure 6:
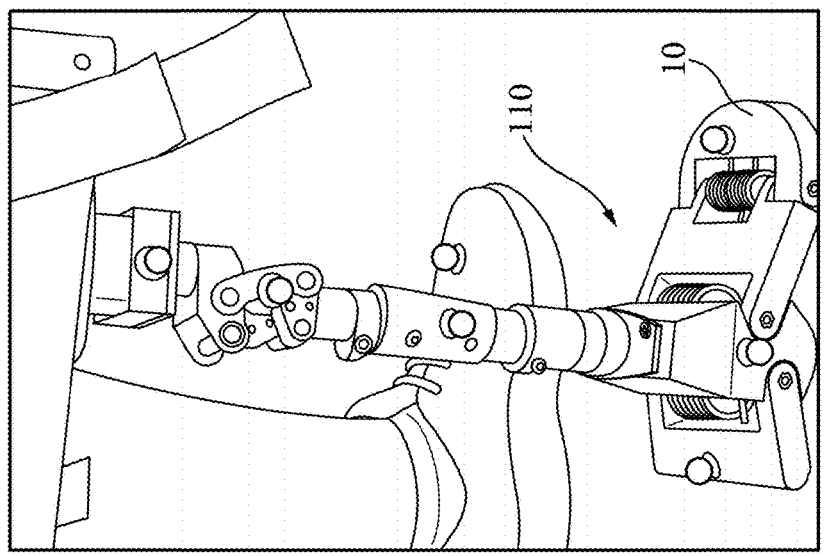
FIG. 6 shows a prosthetic device in the prior art coupled to the prosthetic simulator.

In the illustrated embodiment of FIGS. 1-3, the prosthetic device 10 has a neutral length of 22 cm, 10 cm in width, and 9 cm in height. With a weight between 737.7 g and 887.1 g, the device 10 is heavier than a prosthetic device in the prior art 100 (i.e., the SACH foot, see FIG. 6) that weighs 415.1 g. However, 3D printing the prosthetic device 10 using different materials such as a carbon-fiber nylon composite can reduce the weight in future models.

The prosthetic device 10 has been designed to create distinctly different roll-over shapes (i.e., a gait characteristic that incorporates both kinematics and kinetics). Able-bodied individuals may alter their ankle kinematics in order to maintain their roll-over shape. Amputees, on the other hand, do not have adaptive control over their roll-over shape. The design of the prosthetic device 10 predominantly controls the roll-over shape that the amputee will produce.

Figure 9A:
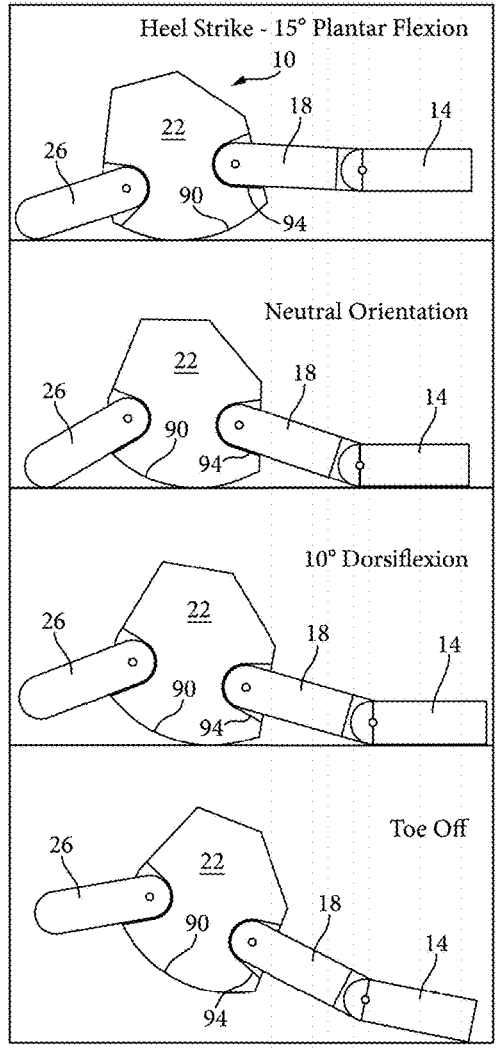
FIG. 9A is a side view of the prosthetic device of FIG. 1, illustrating different positions of the prosthetic device during a gait cycle.
Figure 9B:
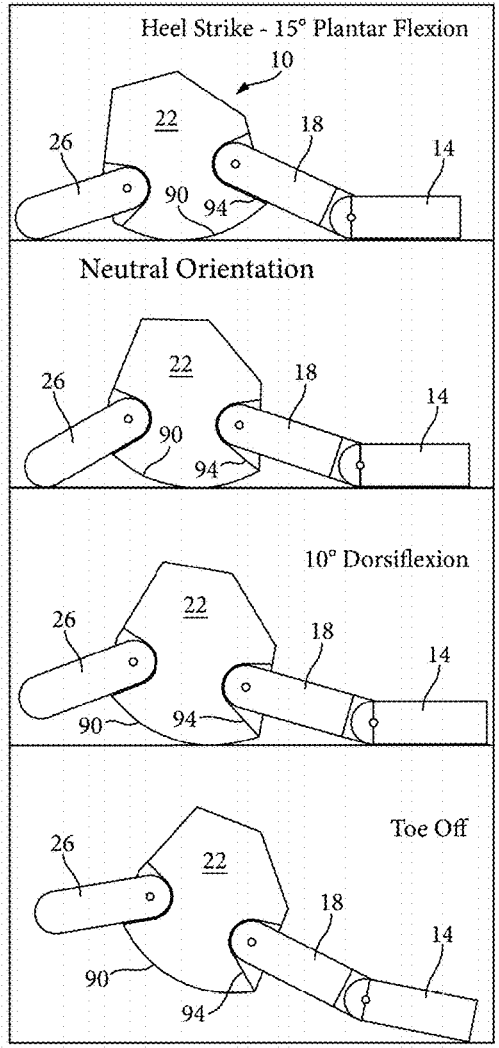
FIG. 9B is a side view of the prosthetic device according to another embodiment, illustrating different positions of the prosthetic device during a gait cycle.
Figure 10A:
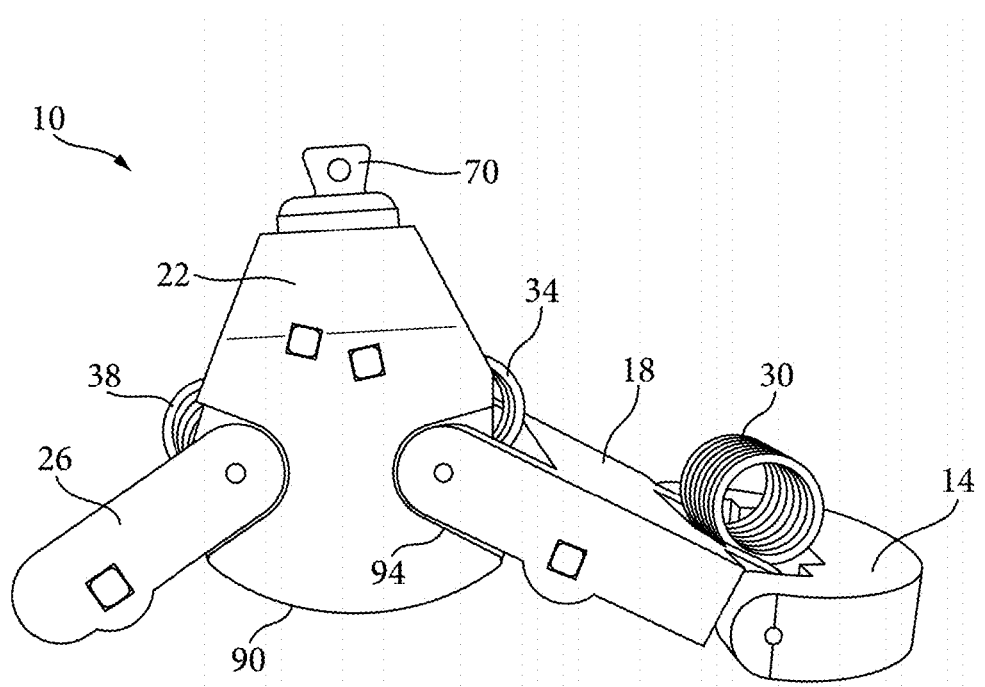
FIG. 10A is a perspective view of the prosthetic device of FIG. 1 in a first position.
Figure 10B:
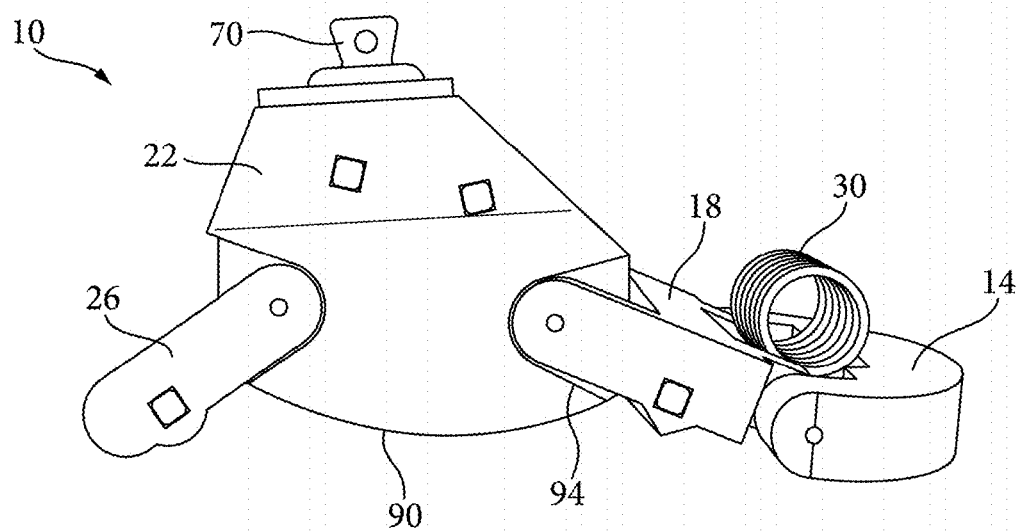
FIG. 10B is a perspective view of the prosthetic device of FIG. 9B in a first position.
Figure 11:
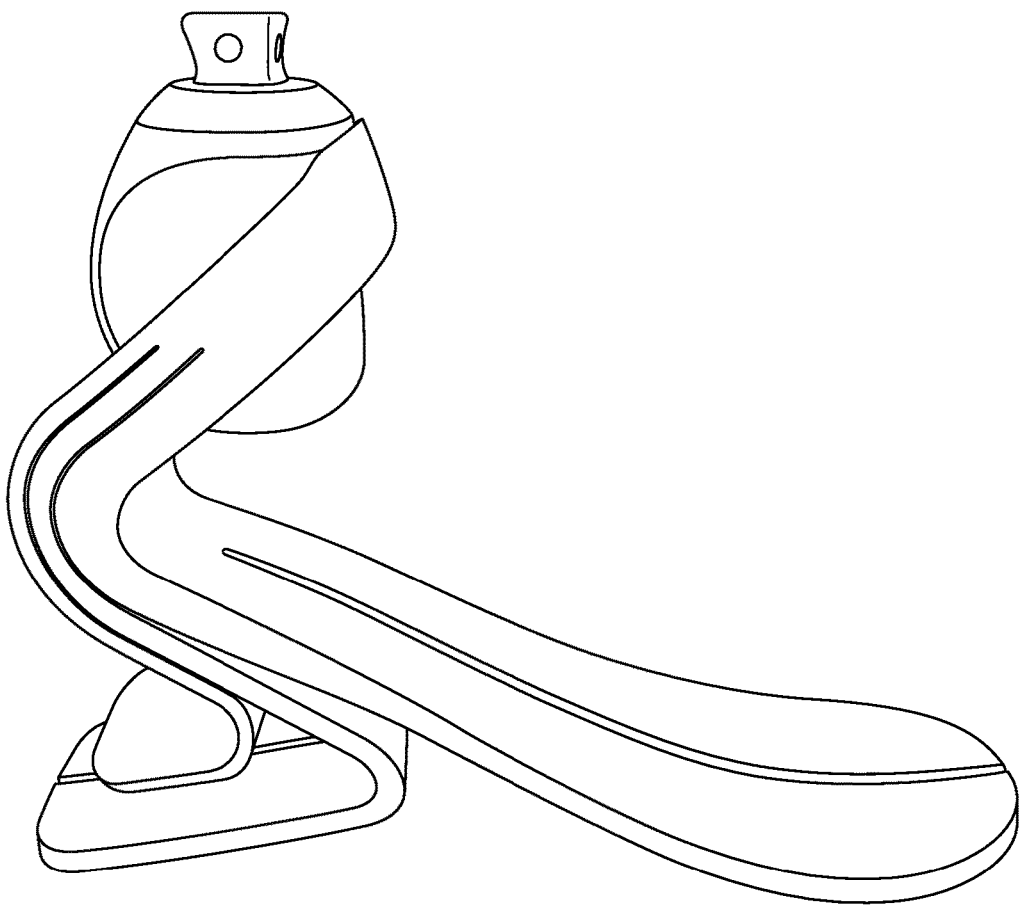
FIG. 11 illustrates a dynamic response ankle-foot.
Figure 12:
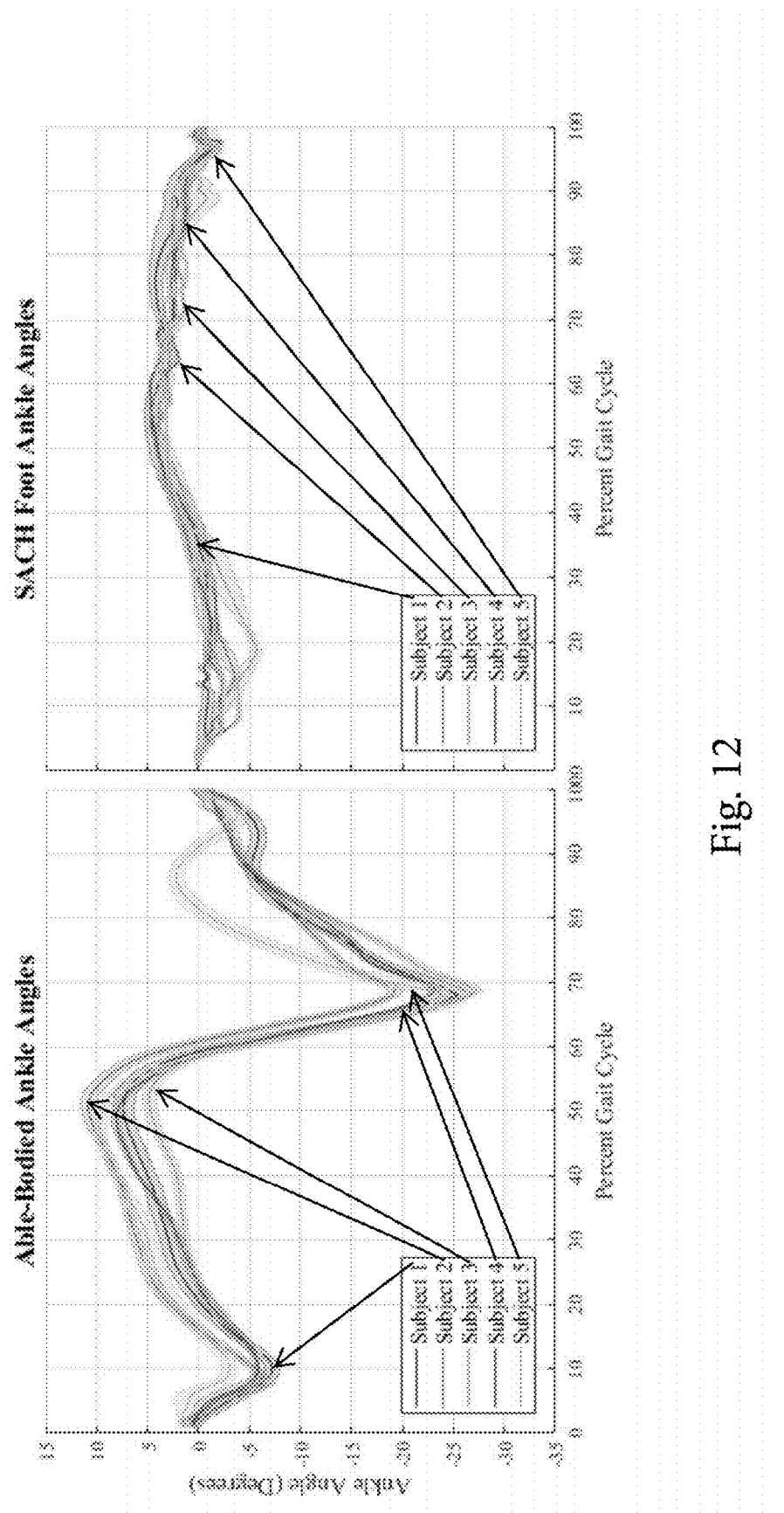
FIG. 12 is a graph that plots the ankle angles of five different test subjects for an able-bodied ankle and for the prosthetic device in the prior art of FIG. 6.
Figure 13:
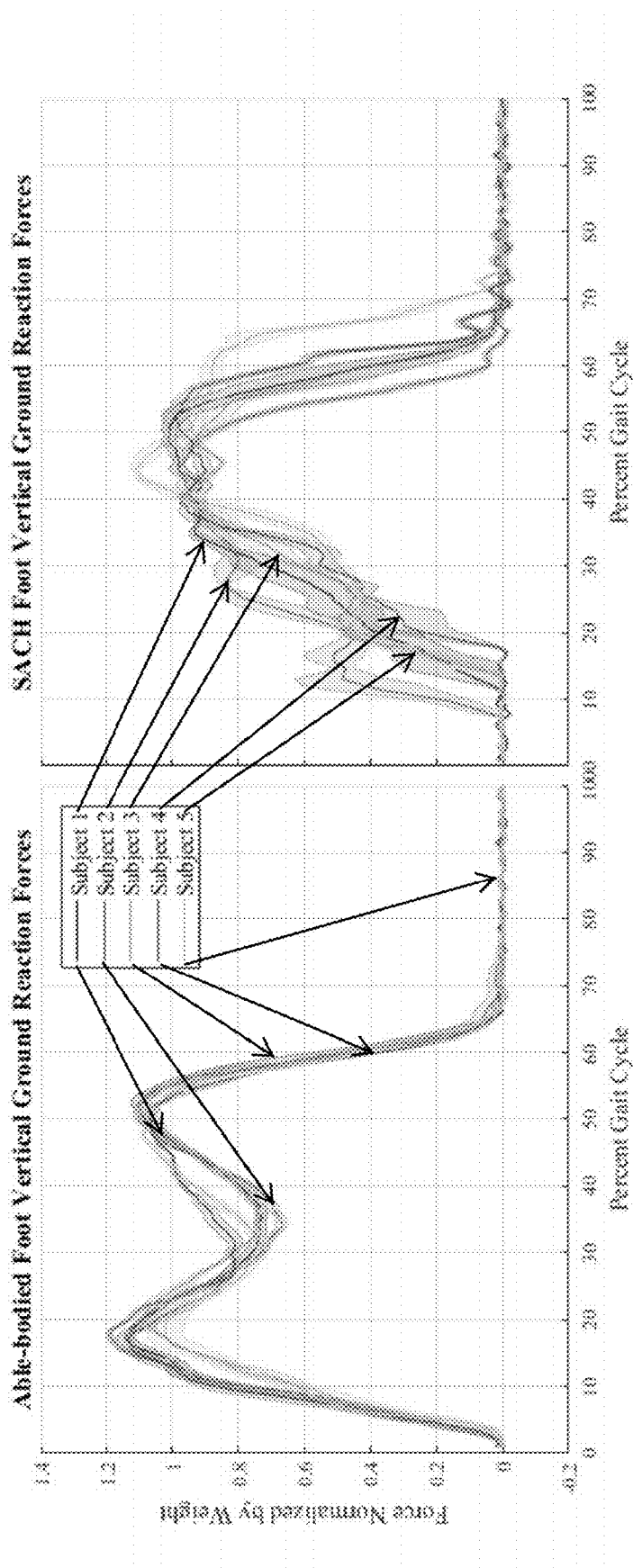
FIG. 13 is a graph that plots vertical ground reaction forces of five different test subjects for an able-bodied ankle and for the prosthetic device in the prior art of FIG. 6.

The embodiment illustrated in FIG. 9A shows the prosthetic device 10 that includes no pretension in the springs 30, 34, 38 in a neutral position (i.e., between plantar flexion and dorsiflexion where the pyramid head 70 is substantially normal to the ground). The embodiment illustrated in FIG. 9B shows the prosthetic device 10 that includes pretension in at least one spring 30, 34, 38 in the neutral position so that energy is stored in the at least one spring 30, 34, 38 at heel strike as opposed to when dorsiflexion begins. As shown in FIG. 10B, the platform 94 of the prosthetic 10 (i.e., where the metatarsal portion 18 rests on the ankle portion 22) is angled fifteen degrees lower (i.e., an end of the platform 94 is closer to the ground) in the illustrated embodiment, than in the embodiment illustrated in FIG. 10A. The change in the position of the platform 94 causes the at least one of the springs 30, 34, 38 to experience a pretension. The heel, the metatarsal portion 18, and the rocker 90 are in contact with the ground during plantar flexion.

A larger roll-over length (e.g., as measured from a heel to a toe) is found to be desirable. In the illustrated embodiment, in order to achieve a larger radius within the dimensions of a normal foot, a center of curvature and a point of contact when the foot is in the neutral position is moved in from of an ankle marker (i.e., toward the toes). The resulting roll-over shape will also have a center of curvature with a forward shift.

Figure 4:
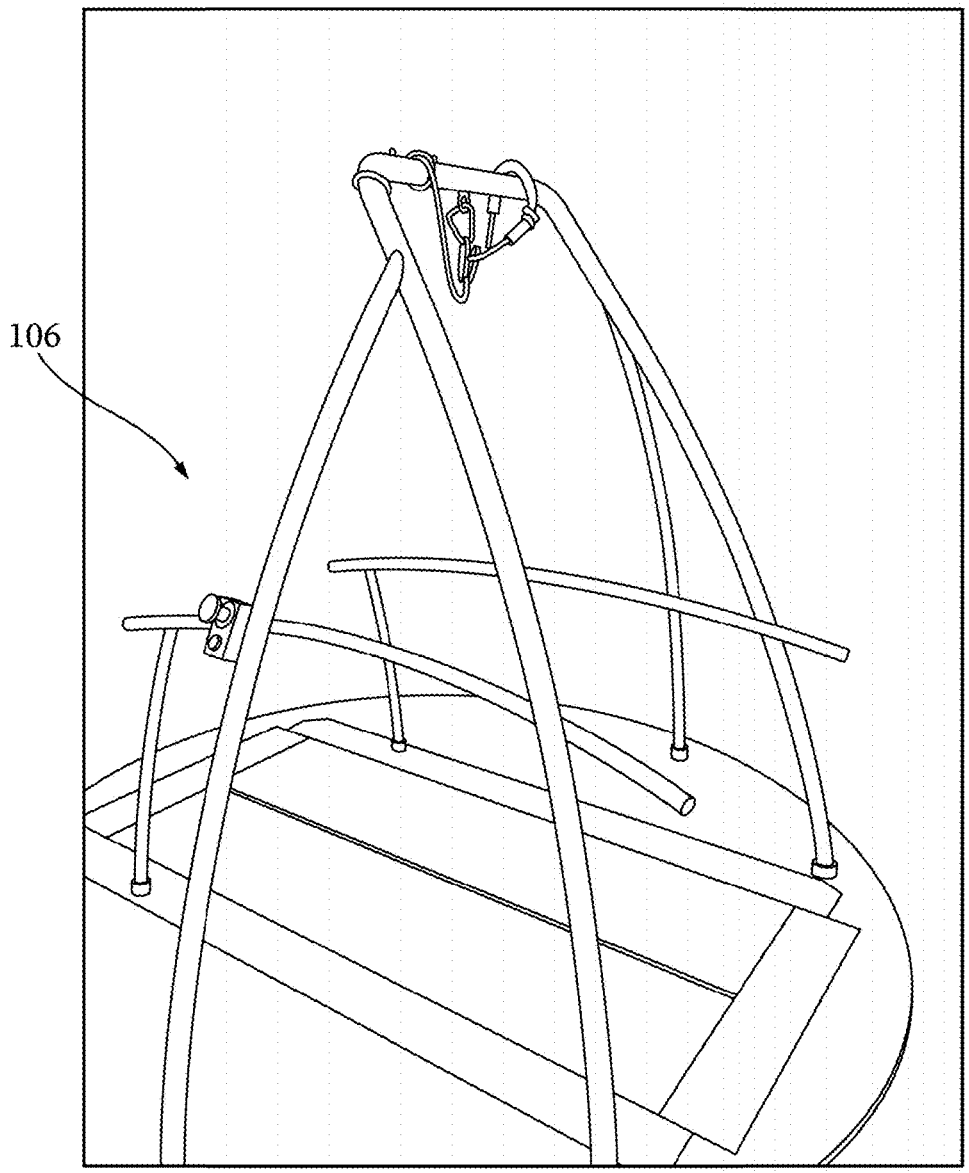
FIG. 4 is a computer assisted rehabilitation environment used to test the prosthetic device of FIGS. 1-3.
Figure 5:
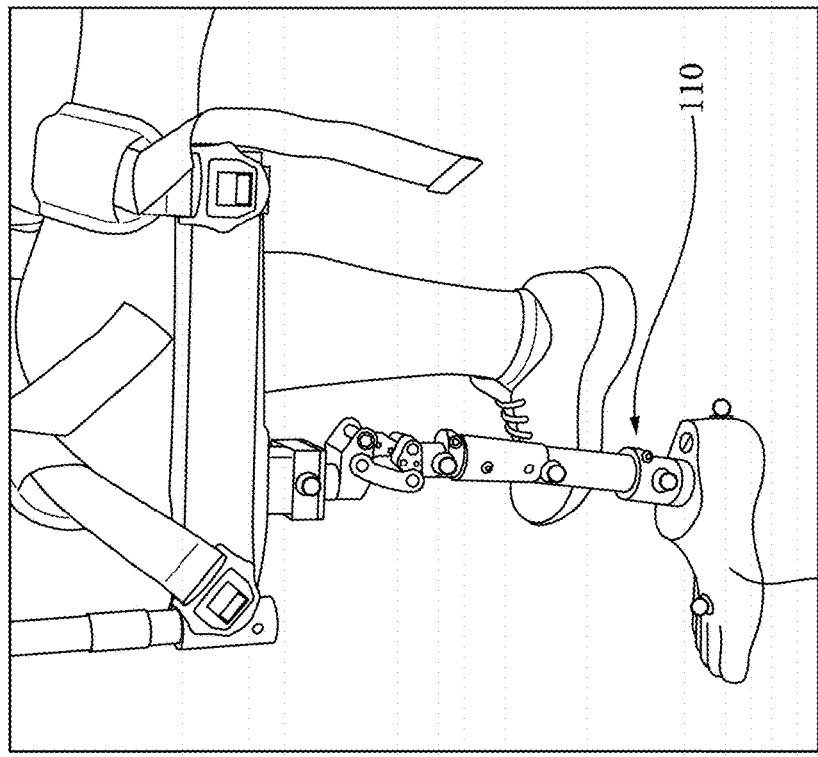
FIG. 5 shows the prosthetic device of FIGS. 1-3 coupled to a prosthetic simulator.

Data was collected using the CAREN 106 (Computer Assisted Rehabilitation ENvironment) shown in FIG. 4 that is equipped with 10 motion capture cameras, a split-belt treadmill with force plates, 180° of projection screens, and a six degree of freedom motion base. The prosthetic device 10 was compared to the conventional SACH foot 100 (see FIGS. 5 and 6) using a prosthetic simulator 110 on an able-bodied individual's right leg. The prosthetic simulator 110 in FIGS. 5 and 6 was assembled from a portion of an iWalk© and a polycentric prosthetic knee. The subject, who weighed 58 kg, walked at a speed of 0.7 m/s for 1 min first using the simulator with the prosthetic device 10, then using the simulator with the SACH foot 100, then walking normally 114. Data from the position coordinates from 18 markers and the magnitude and direction of forces exerted on the treadmill was collected for analysis. Ten steps on the right leg with times within +/−0.3% of the mode step time were chosen and the forces and angles during gait cycle compared.

Figure 7:
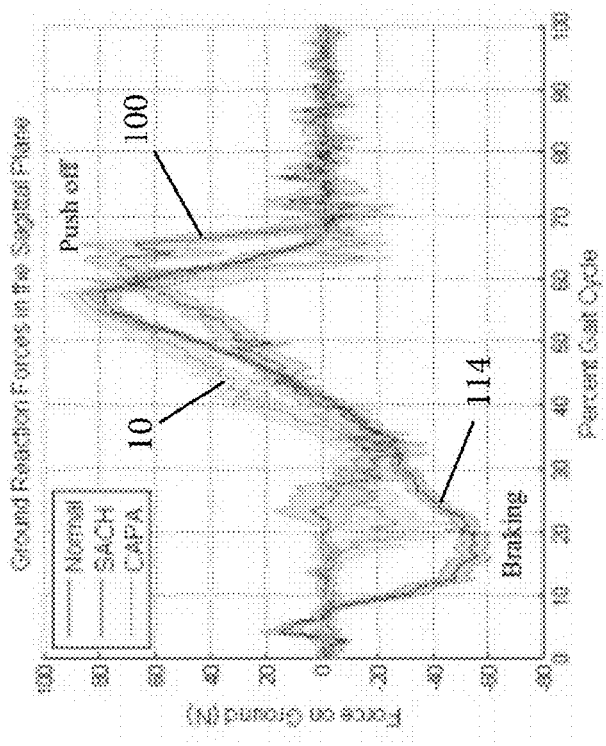
FIG. 7 is a graph that plots the ground reaction forces of the prosthetic device of FIG. 5, the prosthetic device in the prior art of FIG. 6, and an able-bodied person during gait cycle.

The braking and push off forces can be analyzed by looking at GRF (ground reaction forces) exerted horizontally in the front to back direction (z-axis on CAREN 106). FIG. 7 plots ground reaction forces with respect to gait cycle increasing from heel strike to toe off and starting when the heel marker is at its front-most position to when it is at its backmost position. At the beginning of the gait cycle, heel strike is experienced and negative GRF are generated. The step proceeds with push off that produces positive GRF and assists in the forward motion of gait. The gait cycle ends in swing phase with close to zero GRF. FIG. 7 shows that the GRF of the prosthetic device 10 during gait cycle follows more closely to normal gait than the SACH prosthetic foot 100. The average push off force during testing was greater for the prosthetic device 10 (97.7N) compared to the SACH foot 100 (95.9N). It also can be noted from FIG. 7 that the magnitude of the braking force of the prosthetic device 10 and the SACH foot 100 was less than that experienced during normal walking.

Figure 8:
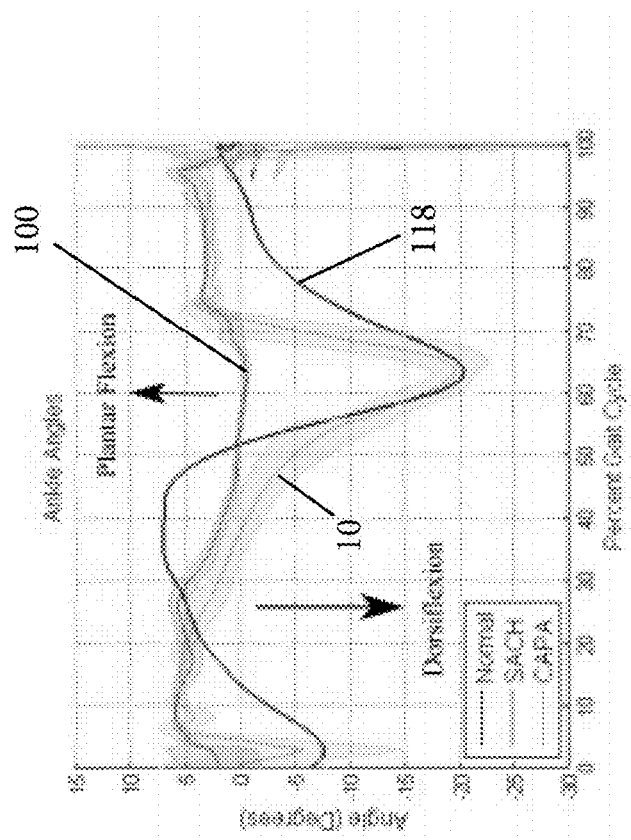
FIG. 8 is a graph that plots the ankle angles of the prosthetic device of FIG. 5, the prosthetic device in the prior art of FIG. 6, and raw ankle data.

The ankle angles were computed from the positions of the toe, ankle, and knee markers. FIG. 8 shows that the prosthetic device 10 exhibits a similar range of motion during gait that an able-bodied individual experiences, from around 15° plantar flexion to 10° dorsiflexion. The results of normal walking were removed from FIG. 8 because the subject exhibited less dorsiflexion and excessive pronation during gait that caused the ankle angles to substantially differ from the well understood ankle angles of an able-bodied individual. Instead, raw ankle angle data 118 collected by another source was plotted to demonstrate typical ankle angles. Gait begins with an initial increase in ankle angle for plantar flexion during heel strike and the angle decreases as the step proceeds reaching minimum dorsiflexion just before push off during which plantar flexion occurs. The prosthetic device 10 was shown to emulate the ankle angles of a healthy gait much better than that of the SACH foot 100 whose ankle angles remained relatively constant throughout the gait cycle.

The GRF experienced while wearing the prosthetic device 10 came closer to emulating normal walking than the SACH foot 100. However, the push off force was only slightly greater for the prosthetic device 10 despite the ESR mechanisms of the springs. Stiffer springs could help achieve a larger push off force. Both the prosthetic device 10 and the SACH foot 100 fell short of replicating the braking forces during the beginning of the gait cycle. However, because the braking force acts against forward motion, high braking forces may inhibit an amputee from producing the necessary forward propulsion from their prosthetic limb. Also, high GRF could cause greater socket forces and lead to discomfort. With regards to the movement in the sagittal and transverse planes that a healthy human ankle experiences, the design of the prosthetic device 10 falls short. Incorporating sagittal and transverse plane movement into the design improves stability and walking on uneven terrain. This has been accomplished by multi-axial prosthetic ankle foot designs that offer a good alternative to the SACH foot 100 for more active amputees. Future models can integrate some of the beneficial aspects of multi-axial designs such as a split foot mechanism to better emulate movement of a healthy human ankle. Also, shock absorption mechanisms can be implemented to improve future models.

This experiment demonstrated the potential of the prosthetic device 10 to be used by lower limb amputees. When compared to the conventional SACH foot 100, the ground reaction forces and ankle angles better mimicked that of a healthy human gait.

In a mathematical model, the prosthetic device 10 (i.e. referred to as "CAPA foot") may be thought of as a rocker with two arms and a toe in the 2-dimensional sagittal plane. Using a rotational velocity of the shank and the geometry of the foot at its neutral position, a series of kinematic equations may be developed to solve for the relative positions of all components during stance phase. When the components are rotated, potential energy is stored in the springs. This creates a resultant force at the point of contact between the arm and the ground. The force distribution is used to find the center of pressure during the step and is then used to plot the roll over shape.

In the mathematical model, during the beginning of the gait cycle the foot is in plantar flexion and the heel component is rotated upward. For a first version of the CAPA foot, only the heel and rocker components are in contact with the ground during plantar flexion. For a second version, the foot component is in contact with the ground as well. Once the shank angle passes the vertical position, the CAPA foot dorsiflexes and only the foot and the rocker is in contact with the ground. The arm geometry is the only difference between the kinematic equations governing the rotation upward of the heel arm versus the foot arm. Therefore, the same kinematic equations can be used. When solving for the ground reaction forces and force distribution, the stiffness of the joint is also adjusted according to the spring constant. The contribution of the toe is disregarded.

Figure 16:
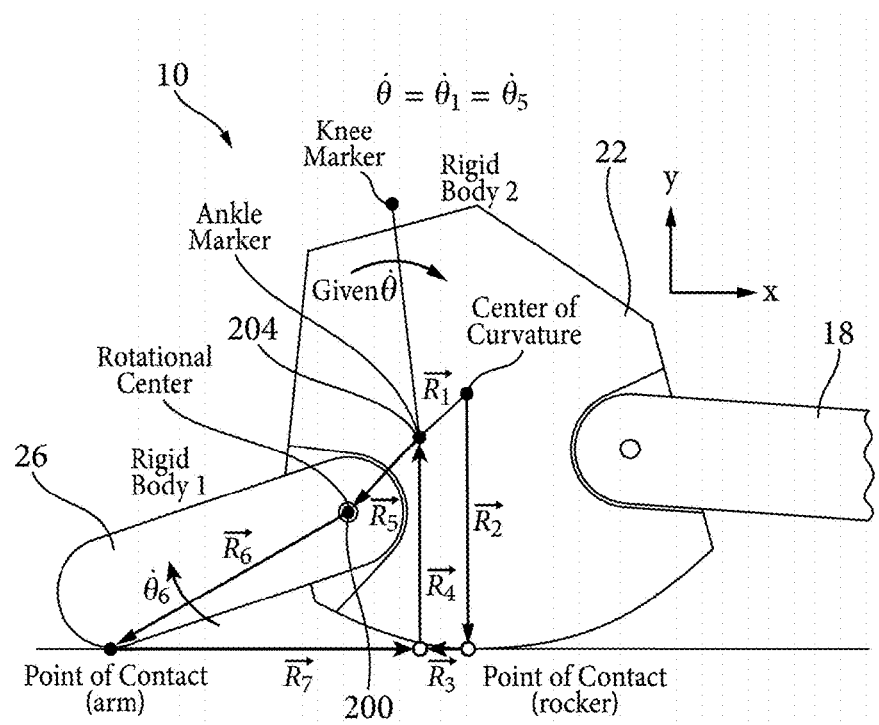
FIG. 16 is a representation of vector loops on the prosthetic device of FIG. 5 during a step.
Figure 17:
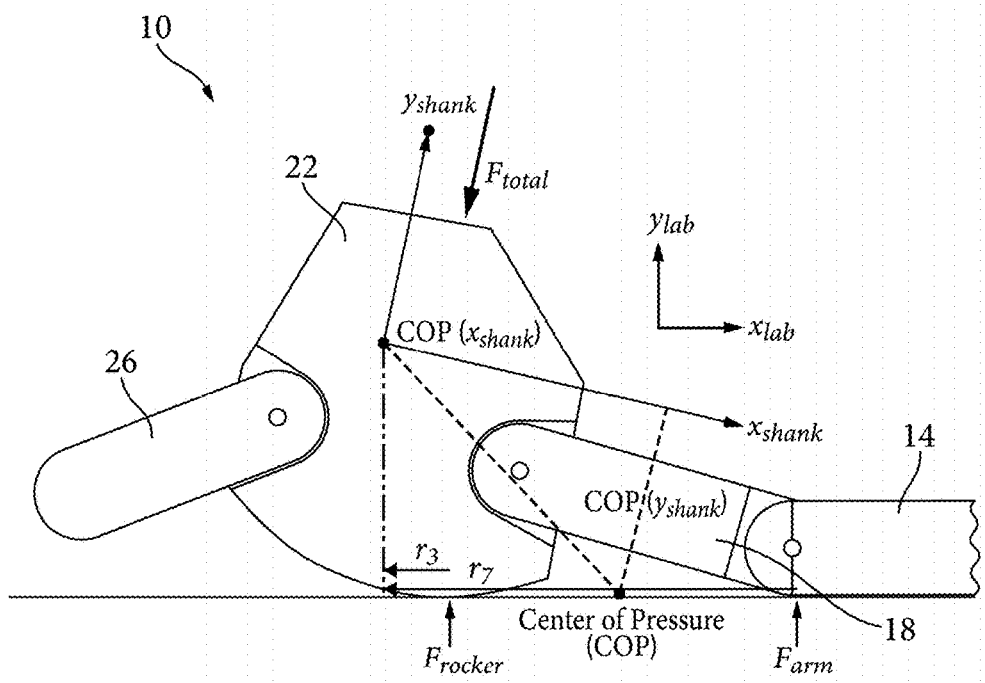
FIG. 17 is a force diagram on the prosthetic device of FIG. 5.

In the mathematical model, and as shown in FIG. 16, points on a rocker or ankle portion 22 and an arm (e.g., a calcaneus portion 26) can be connected by two loops of vectors. These points and vectors can be considered part of either a first rigid body (e.g., a calcaneus portion 26) or a second rigid body (e.g., an ankle portion 22). The first rigid body 26 will rotate about a rotational center 200, and the second rigid body 22 will rotate about an ankle marker 204 with the rotation velocity of a shank (not shown). Geometrically fixed vector lengths and points are shown in black and unknown vector lengths and angles are shown in blue. The fixed lengths and angles are shown in FIG. 18 with the angles defined from the positive x-axis.

At every position of the CAPA foot, each of the two vector loops shown in FIG. 16 must make one full circle meaning that each vector sum must equal to 0. Given the lengths of the vectors when the prosthetic device 10 is in the neutral orientation, the vector velocities can be used to solve for all remaining positions of the vectors. By applying the fixed geometries listed shown in FIG. 18 and a relationship stating that $\dot{\theta}=\dot{\theta}_1=\dot{\theta}_5$, the equations from FIG. 19 reduce to the following two equations:

$$\dot{r}_3 = \frac{-r_1\dot{\theta}\sin(\theta_1)}{\cos(\theta_3)}$$

$$\dot{r}_4 = -r_1\dot{\theta}\cos(\theta_1)$$

The equations from FIG. 20 reduce to the following two equations:

$$\dot{\theta}_6 = \frac{r_5\dot{\theta}\cos(\theta_5) + \dot{r}_4}{-r_6\sin(\theta_6)}$$

$$\dot{r}_7 = \frac{r_5\dot{\theta}\sin(\theta_5) + r_6\dot{\theta}_6\sin(\theta_6)}{\cos(\theta_7)}$$

Given the lengths of the vectors when the foot is in the neutral orientation, the vector velocities can be used to solve for all remaining positions of the vectors. The same parameters are used in the ankle loop equations given in FIG. 20 and the equations derived from FIG. 20 to describe the movement of the ankle portion 22 throughout the entire step. However, different values for $r_5$, $r_6$, and $\theta_7$ are used depending on the arm (the metatarsal portion 18 or the calcaneus portion 26) in contact with the ground. For example, when the shank passes the vertical position, the heel arm is not in contact with the ground anymore and there will be no resultant force between the heel arm and the ground. When the value of $r_3$ equals zero and the center of curvature crosses the ankle marker, the value of $\theta_3$ switches between 0 and 180 degrees.

When either of the arms (e.g., the calcaneus portion 26 or a metatarsals portion 18) is bent upward, biasing members or springs 30, 34, 38 (FIGS. 1-3) are compressed at an angle between $\theta_6$. The resultant force $F_{arm}$ (given by $F_{arm}=K*(\dot{\theta}_6-\dot{\theta})$) will push against the ground at the point of contact between the arm 18, 26 and the ground. The remaining forces $F_{rocker}$ will occur at the point of contact between the ankle portion 22 and the ground. $F_{rocker}$ is determined by subtracting $F_{arm}$ from $F_{total}$, where $F_{total}$ is an experimentally controlled value. The difference between the x direction location of the center of pressure and the ankle marker is given by the following equation:

$$x_{lab} - x_{ankle} =$$
$$\frac{-1}{F_{total}} * [(F_{rocker}r_3\cos(\theta_3)) + (F_{rocker}r_7\cos(\theta_7))_{heel} + (F_{rocker}r_7\cos(\theta_7))_{foot}]$$

where $\theta_3$ or $\theta_7$ are 0 or 180 degrees. These points can then be plotted to form the roll over shape.

Figure 14:
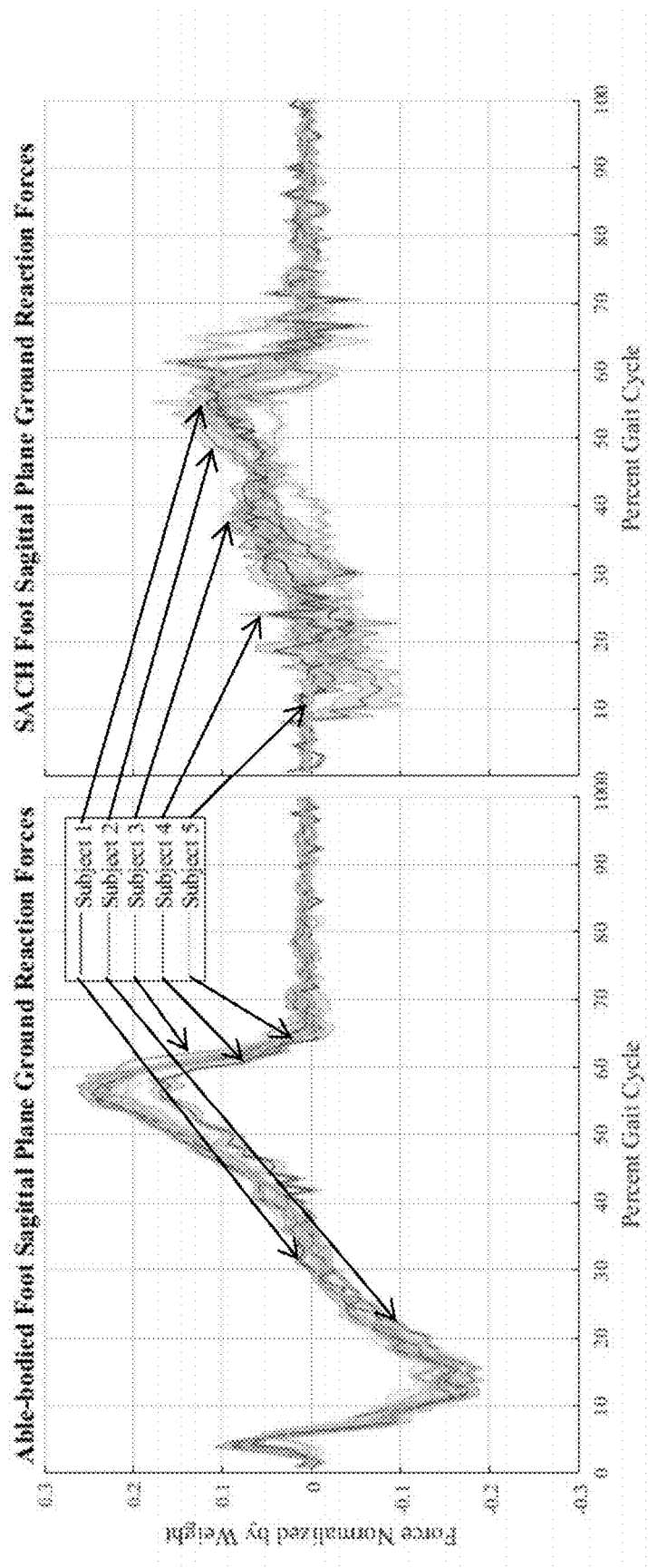
FIG. 14 is a graph that plots sagittal plane ground reaction forces of five different test subjects for an able-bodied ankle and for the prosthetic device in the prior art of FIG. 6.
Figure 15:
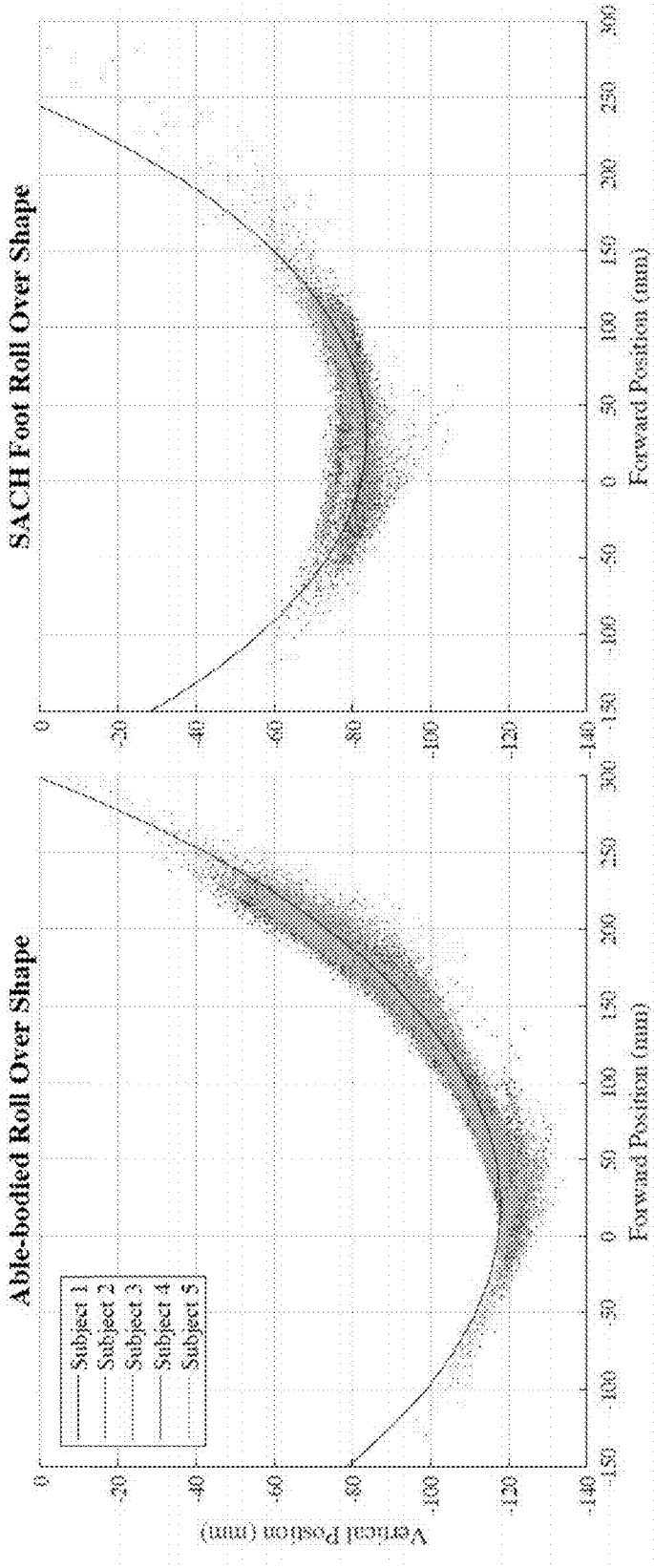
FIG. 15 is a graph that plots the roll-over shape of five different test subjects for an able-bodied ankle and for the prosthetic device in the prior art of FIG. 6.

The quasi-stiffness of the human ankle can be evaluated by measuring the slope of the ankle angle versus ankle moment graph. An alternative way of determining the joint stiffness required by the CAPA foot is to look at the discrepancy between the gait of an able-bodied individual and the gait of the same individual wearing the SACH foot that provides very little push-off. FIG. 14 shows the discrepancy to be approximately 10% the individual's body weight. The average participant in the study weighed 72.22 kg so the CAPA foot must reach 70.8N of force at 10 degrees dorsiflexion. Therefore, a rotational stiffness of $$7.08 \frac{N}{\deg}$$

was used to guide the effective rotational stiffness values given in FIG. 21.

As shown in FIG. 22, after determining the spring constant, the geometries of the CAPA foot can be chosen to produce the desired roll over shape (e.g., ability to personalize to a specific roll over shape). Additionally, increasing the stiffness at either the heel or toe lengthens the roll over shape. Increasing the distance $r_1$ between the ankle marker and the center of curvature of the ankle 22 by using a larger radius will cause the point of contact between the ankle 22 and the ground to move more during the step, which will result in a flatter and longer roll over shape. A length of the arm piece (e.g., the calcaneus portion 26) may also be increased. Increasing the length $r_6$ of the arm piece 18, 26 will increase a distance of a point of contact between the arm and the ground and the ankle marker causing the center of pressure to move further forward and also causing the roll over shape to lengthen.

Although the invention has been described in detail with reference to certain preferred embodiments, variations and modifications exist within the scope and spirit of one or more independent aspects of the invention as described.

What is claimed is:

1. A prosthetic device comprising:
a phalanges portion;
a metatarsals portion that is movably coupled to the phalanges portion at a first connection point;
an ankle portion that is movably coupled to the metatarsals portion at a second connection point spaced apart from the first connection point;
and a calcaneus portion that is movably coupled to the ankle portion at a third connection point spaced apart from the first and second connection points;
wherein at least one biasing member rotatably couples the metatarsals portion to the phalanges portion, at least one biasing member rotatably couples the metatarsals portion to the ankle portion, and at least one biasing member rotatably couples the calcaneus portion to the ankle portion;
wherein each of the at least one biasing members is a torsion spring.

2. The prosthetic device of claim 1 wherein the ankle portion is configured to be coupled to another prosthetic structure.

3. The prosthetic device of claim 1 wherein the first connection point includes a first recess, the second connection point includes a second recess, and the third connection point includes a third recesses, and wherein the first biasing member is disposed within the first recess, the second biasing member is disposed within the second recess, and the third biasing member is disposed within the third recess.

4. The prosthetic device of claim 1 wherein at least one of the phalanges portion, the metatarsals portion, or the calcaneus portion is a flat plate.

5. A prosthetic device comprising:

a phalanges portion;

a metatarsals portion coupled to the phalanges portion at a first connection point; an ankle portion coupled to the metatarsals portion at a second connection point spaced apart from the first connection point;

a calcaneus portion coupled to the ankle portion at a third connection point spaced apart from the first and second connection points;

and at least one biasing member configured to bias at least one of the phalanges portion, the metatarsals portion, the ankle portion, or the calcaneus portion in a rotational direction;

wherein the at least one biasing member includes a first biasing member that rotatably couples the metatarsals portion to the phalanges portion, a second biasing member that rotatably couples the metatarsals portion to the ankle portion, and a third biasing member that rotatably couples the calcaneus portion to the ankle portion;

wherein the at least one biasing member is a torsion spring.

6. The prosthetic device of claim 5 wherein the ankle portion includes a rounded portion extending between the metatarsals portion and the calcaneus portion.

7. A prosthetic ankle foot comprising:

an ankle portion including a first end with a connector and a second end with a rocker having a curved surface configured to contact the ground, the first end opposite the second end;

a metatarsals portion rotatably coupled to the ankle portion by a first biasing member;

a calcaneus portion rotatably coupled to the ankle portion by a second biasing member, the metatarsals portion and the calcaneus portion coupled to the ankle portion on opposite sides of the rocker;

and a phalanges portion rotatably coupled to the metatarsals portion by a third biasing member;

wherein each of the first, second, and third biasing members is a torsion spring.

8. The prosthetic device of claim 7 wherein the connector is configured to be coupled to another prosthetic device.

9. The prosthetic device of claim 7 wherein at least one of the first, second, and third biasing members is configured to be under pretension while the connector is substantially normal to the ground.

* * * * *